(12) United States Patent
Mailyan

(10) Patent No.: US 7,357,633 B2
(45) Date of Patent: Apr. 15, 2008

(54) DEVICE FOR CORRECTION OF THE FORM OF UPPER JAW

(75) Inventor: Pavel D. Mailyan, Yerevan (AM)

(73) Assignee: Mayadontics, LLC, San Rafael, CA (US)

( * ) Notice: Subject to any disclaimer, the term of this patent is extended or adjusted under 35 U.S.C. 154(b) by 147 days.

(21) Appl. No.: 11/327,211

(22) Filed: Jan. 7, 2006

(65) Prior Publication Data

US 2007/0037112 A1 Feb. 15, 2007

(30) Foreign Application Priority Data

Aug. 9, 2005 (AM) .................................. 20050148

(51) Int. Cl.
*A61C 3/00* (2006.01)

(52) U.S. Cl. ........................................................ 433/7
(58) Field of Classification Search ................... 433/6, 433/7, 18, 24

See application file for complete search history.

(56) References Cited

U.S. PATENT DOCUMENTS

| | | | | |
|---|---|---|---|---|
| 1,142,467 A | | 6/1915 | Walker | 433/21 |
| 4,026,023 A | * | 5/1977 | Fisher | 433/7 |
| 4,028,808 A | * | 6/1977 | Schwartz | 433/7 |
| 4,468,196 A | | 8/1984 | Keller | 433/24 |
| 4,573,914 A | * | 3/1986 | Nord | 433/18 |

(Continued)

FOREIGN PATENT DOCUMENTS

AM 197 11/1996

(Continued)

OTHER PUBLICATIONS

A. A. Kolesov "Stomatology of childhood" Moscow 1970, pp. 452, 453 (description of Fig. 106).

(Continued)

*Primary Examiner*—Cary E. O'Connor
(74) *Attorney, Agent, or Firm*—Joshua D. Isenberg; JDI Patent

(57) ABSTRACT

The invention relates to the medicine, in particularly, in orthodontics, and can be used during the correction of the form of upper jaw, namely, dental, alveolar and basal arches. The task of the group of inventions is to ensure increased functionalities of the devices for correction of the form of upper jaw, namely, dental alveolar and basal arches. The group of inventions has fastening elements, which are fastened on teeth of dentition's lateral segments and executed in the form of metal wireframes clasping teeth of dentition's lateral segments, and connected with two plates located on both sides of median palatine suture and connected with each other by the metal wire palatal power element or elements. In a first variant of the group of inventions, the plates are connected with the fastening elements through springs. The second and third variants of the group of inventions additionally have fastening elements, which are mounted on teeth of dentition's frontal segment and executed in the form of metal wireframe too. In the second variant of the group of inventions the plates are connected with fastening elements of lateral segments through springs, and a fastening element of frontal segment is connected with a metal wire palatal power element by springs. In a third variant of the group of inventions fastening elements are connected with each other and plates by a palatal arch through springs.

3 Claims, 2 Drawing Sheets

U.S. PATENT DOCUMENTS

| | | | |
|---|---|---|---|
| 4,637,796 A | | 1/1987 | Korn .............................. 433/7 |
| 4,976,614 A | * | 12/1990 | Tepper ......................... 433/18 |
| 5,002,485 A | * | 3/1991 | Aagesen ........................ 433/7 |
| 5,087,196 A | | 2/1992 | Polanco ........................ 433/21 |
| 5,096,416 A | * | 3/1992 | Hulsink ......................... 433/6 |
| 5,376,001 A | * | 12/1994 | Tepper ......................... 433/6 |
| 5,507,638 A | * | 4/1996 | Strazielle et al. .............. 433/6 |
| 5,580,243 A | | 12/1996 | Bloore ........................... 433/6 |
| 5,829,970 A | | 11/1998 | Yousefian ...................... 433/7 |
| 6,032,677 A | | 3/2000 | Blechman ................... 128/899 |
| 6,033,216 A | * | 3/2000 | Souris ............................ 433/7 |
| 6,435,871 B1 | | 8/2002 | Inman ............................ 433/7 |
| 7,192,281 B2 | | 3/2007 | Mailyan ..................... 433/215 |
| 2003/0104335 A1 | | 6/2003 | Chung ......................... 433/18 |
| 2004/0013993 A1 | | 1/2004 | Ito ................................. 433/6 |
| 2005/0019720 A1 | | 1/2005 | Harima ........................ 433/18 |

FOREIGN PATENT DOCUMENTS

| | | |
|---|---|---|
| AM | 199 | 11/1996 |
| AM | 511 | 3/1999 |
| AM | 512 | 3/1999 |
| AM | 514 | 3/1999 |
| SU | 848020 | 7/1981 |
| WO | WO 2005/048868 | 6/2005 |

OTHER PUBLICATIONS

Kishinev, *Directory on Orthodontics*, p. 178 (description of Fig. 27) and pp. 179, 179, 181, 182 (description of Fig. 28), 188 and 189.

U.S. Appl. No. 11/327,209, to Pavel D. Mailyan, filed Jan. 7, 2006.

U.S. Appl. No. 11/327,210, to Pavel D. Mailyan, filed Jan. 7, 2006.

U.S. Appl. No. 11/327,212, to Pavel D. Mailyan, filed Jan. 7, 2006.

Office Action of U.S. Appl. No. 11/327,209 issued as US Patent 7,192,281.

The International Search Report and "The Written Opinion of the International Searching Authority" for International application No. PCT/US2006/028793 (MYD-1234/PCT).

\* cited by examiner

DEVICE FOR CORRECTION OF THE FORM OF UPPER JAW

CROSS REFERENCE TO RELATED APPLICATIONS

This application is related to commonly assigned co-pending U.S. patent application Ser. No. 11/327,212 to Pavel D. Mayilyan entitled "DEVICE FOR CORRECTION OF THE FORM OF DENTAL ALVEOLAR ARCH",which is filed concurrently herewith and which is incorporated herein by reference. This application is also related to commonly assigned co-pending U.S. patent application No. 11/327,209 to Pavel D. Mayilyan entitled "METHOD FOR STIMULATION OF GROWTH OF MISSiNG TISSUES OF JAW DEFECTS AND A DEVICE FOR ITS REALIZATION", which is filed concurrently herewith and which is incorporated herein by reference. This application is also related to commonly assigned co-pending U.S. patent application No. 11/327,210 to Pavel D. Mayilyan entitled "METHOD FOR CORRECTION OF THE FORM OF DENTAL ALVEOLAR ARCH", which is filed concurrently herewith and which is incorporated herein by reference.

FIELD OF THE INVENTION

The invention relates to the medicine, in particularly, in orthodontics, and can be used during the correction of the form of upper jaw, namely, dental, alveolar and basal arches.

BACKGROUND

It's known a Derichsweiler's nonremovable orthodontic device for accelerated rupture of a median palatine suture, constituting a plastic basis with a screw and metal reinforcements, free ends of which are rigidly fastened with rings or corona in the region of lateral teeth (see, Khoroshilkina F. Y., Maligin Yu. M. "Fundamentals of designing and technology of manufacturing of orthodontic devices", Publishing House "Medicine" 1977, page 97, FIG. 35).

The design of the device provides stability of installation in a cavity of a mouth, however being nonremovable it facilitates to development of inflammatory diseases of the mucous tunic.

It's also known an orthodontic device for accelerated rupture of a median palatine suture, containing a nonremovable basic parts in the form of rings or corona, which are rigidly disposed on teeth of dentition's lateral segments and connected with each other through vestibular arches and have fixing units executed in the form of vertically disposed tubes soldered on their lingual surface, and a removable part constituting a plastic basis with a screw and metal reinforcements, the free ends of which are bent and mounted in the vertically disposed tubes (see, Khoroshilkina F. Y., Maligin Yu. M. "Fundamentals of designing and technology of manufacturing of orthodontic devices", Publishing House "Medicine", 1977, page 98, FIG. 36) However, above described devices are insufficiently convenient in usage, their removal and installation in the cavity of mouth are possible only at direct participation of the doctor—orthodontist.

It's also known an orthodontic device for accelerated rupture of the median palatine suture (invention patent of the RA No 511 IPC[5] A61C 7/36, 1999.) which favourably differs from analogues by that being removable it provides conditions for as much as possible simplified removal and installation of the device, simultaneously providing the stability of the device.

The device consists of removable and nonremovable parts. The nonremovable parts constitute orthodontic rings, which have fixing units and are rigidly fastened on teeth of dentition's lateral segments and connected with each other through vestibular arches. The removable part contains basic plates, which have vestibular arches and are located on both sides of median palatine suture, and a power element in the form of soldered springs connecting basic plates.

The mentioned design is chosen as a closest analogue for variants of the proposed device. The designs of the closest analogue as well as analogues do not provide effective correction of the configuration (geometry) of palatal fornix, simultaneous corpus (bodily) shifting of teeth and correction of their axial position. Moreover, the designs do not provide correction of the form of dental alveolar arch in a frontal section.

The task of the group of inventions is to ensure increased functionalities of devices for correction of the form of upper jaw, namely, dental alveolar and basal arches.

SUMMARY

In accordance with a first variant of execution of the device, the put task is solved that in the known technical solution containing fastening elements, which are fastened on teeth of dentition's lateral segments and connected with two plates located on both sides of median palatine suture and connected with each other by a metal wire palatal power element, according to the invention fastening elements are executed in the form of metal wireframes clasping teeth of dentition's lateral segments and a connection of fastening elements with plates is carried out through springs.

In accordance with a second variant of execution of the device, the put task is solved that in the known technical solution containing fastening elements, which are fastened on teeth of dentition's lateral segments and connected with two plates located on both sides of median palatine suture and connected with each other by a metal wire palatal power element, according to the invention the design additionally contains a fastening element mounted on teeth of dentition's frontal segment, fastening elements are executed in the form of metal wireframes clasping teeth of dentition's segments, the plates are connected with fastening elements of lateral segments through springs, and a fastening element of frontal segment is connected with a metal wire palatal power element by springs.

In accordance with a third variant of execution of the device, the put task is solved that in the known technical solution containing fastening elements, which are fastened on teeth of dentition's lateral segments and connected with two plates located on both sides of median palatine suture and connected with each other by a metal wire palatal power element, according to the invention the design additionally contains a fastening element mounted on teeth of dentition's frontal segment, fastening elements are executed in the form of metal wireframes clasping teeth of dentition's segments and connected with each other and plates by a palatal arch through springs.

BRIEF DESCRIPTION OF THE DRAWINGS

A first variant of the orthodontic device for correction of the form of upper jaw is represented on FIG. 1.

A cross-section view of the device, according to the first variant of execution is represented on FIG. 2.

Figure 3:
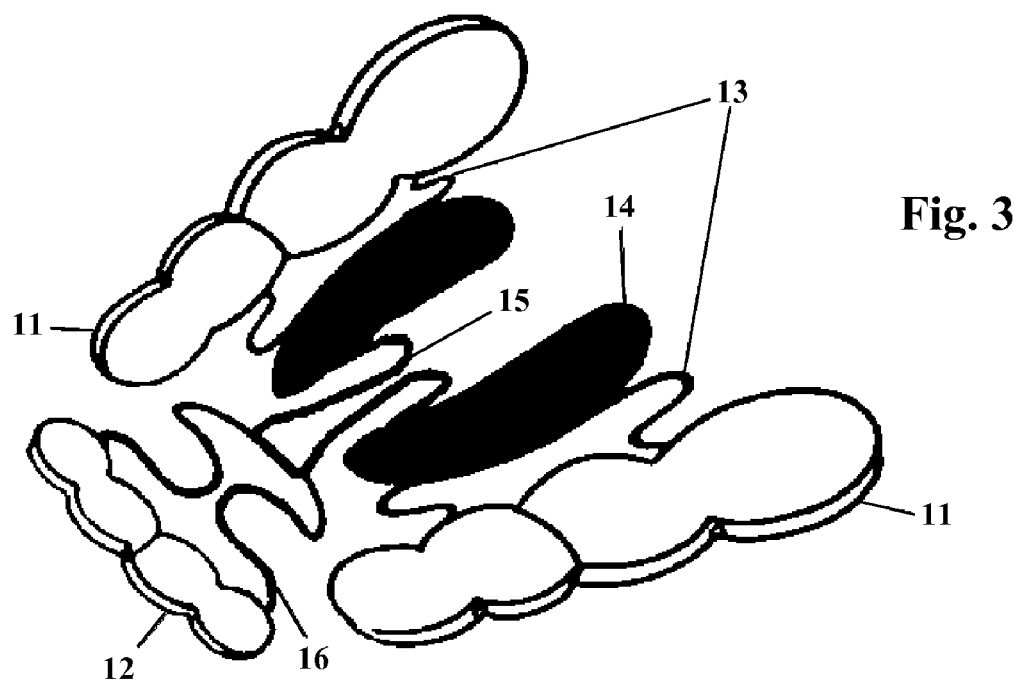
Figure 4:
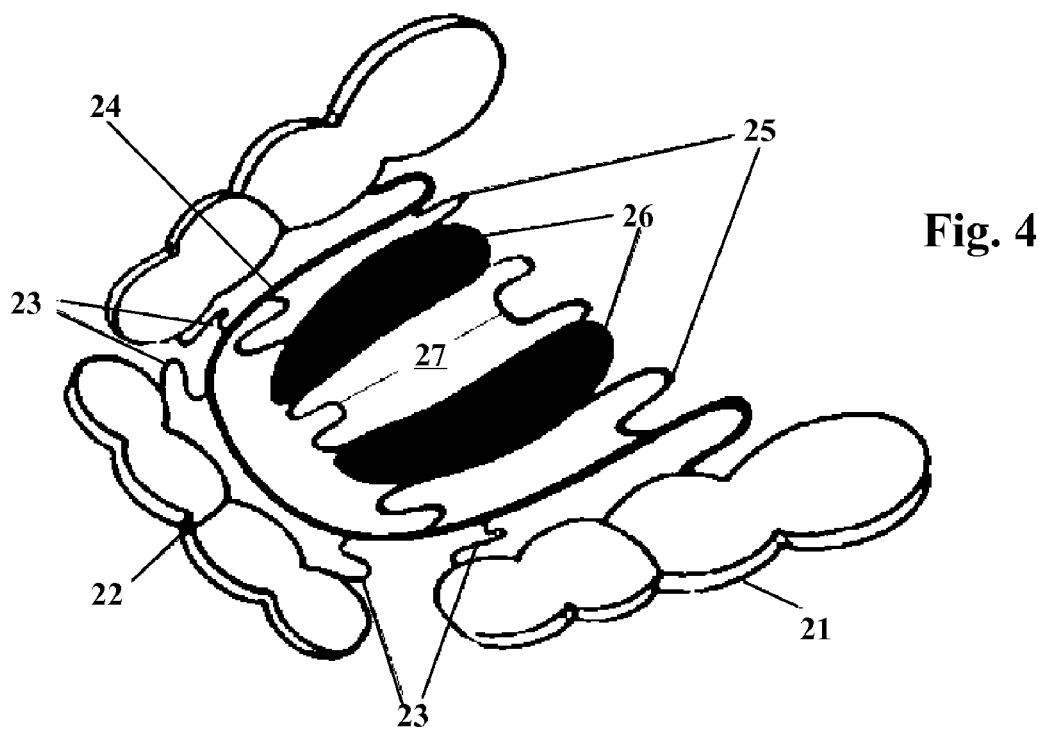

A second variant of the device execution is represented on FIG. 3 and a third variant of the device execution is represented on FIG. 4.

DETAILED DESCRIPTION

In clinical practice frequently are encountered hypopisia and deformation of the upper jaw, the reasons of which could be derangement of mineral metabolism (rickets, dyspepsia) in early childhood, infectious and chronic diseases, dysphagia, dysphasia, disphrasia, early loss of temporary or permanent teeth, disorder of chewing and facial muscles (para function) etc.

In the case of significant constriction of dental, alveolar and basal arches that mostly occurs in the case of high-grade rickets, the cupula of a palate usually has a double fundus.

It is well known that bone tissue is a viscous-elastic medium, the elasticity of which considerably rises at it growth.

Taking into account the above-mentioned, a device has been designed so that at a correction of convex parts of the palatal fornix to combine the influence of plates on them with the rupture of the median palatine suture and the growth of a dental alveolar process. Namely, above and below the convex parts of the palatal fornix a zone of growth of the bone tissue (zone with the increased elastic properties of the bone tissue) is formed. The influence of plates on convex parts of the palatal fornix and presence of two zones with the increased elastic properties of the bone tissue allows to considerably increase the efficiency of correction of the form of cupula of a palate.

Figure 1:
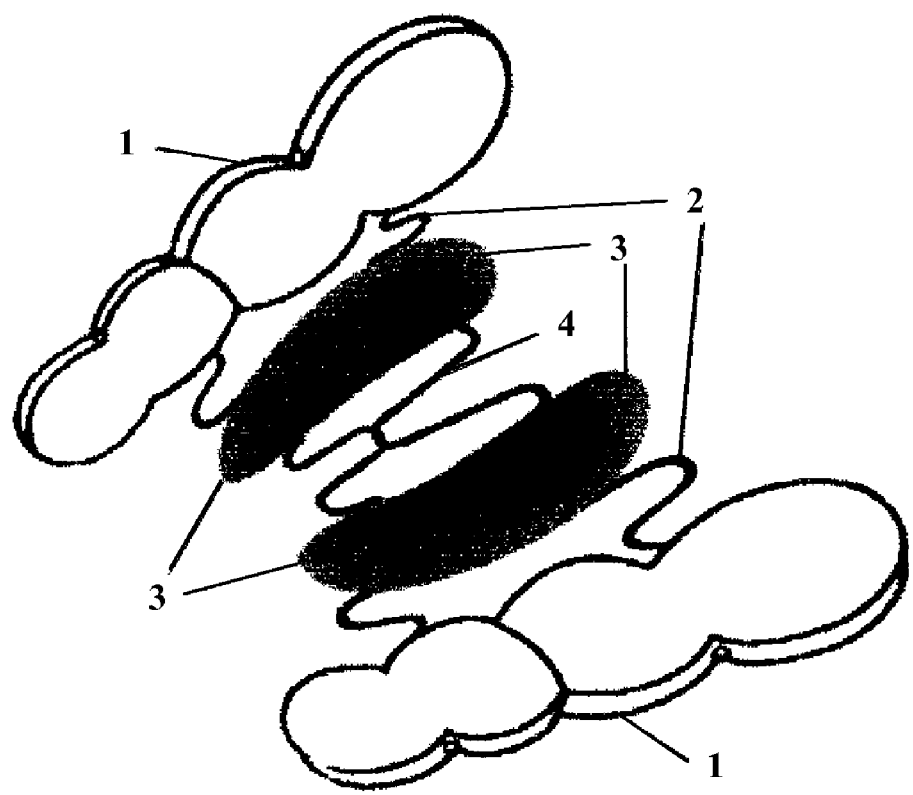
Figure 2:
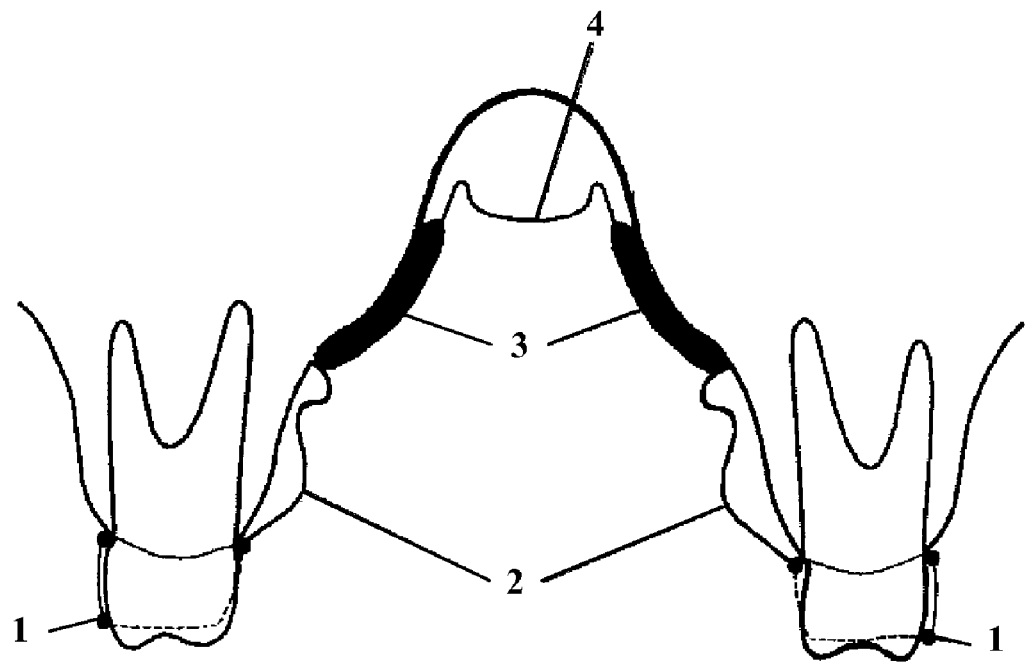

A device for correction of the form of upper jaw in accordance with a first variant consists of fastening elements (1) which are executed in the form of metal wireframes clasping teeth of dentition's lateral segments. Plates (3) are fastened on orthodontic springs (2) soldered to the fastening elements (1). Plates (3) are located on both sides of median palatine suture on convexes of the palatal fornix (see. FIG. 2) and connected with each other by a metal wire palatal power element (4), which may be executed, in particular, in the form of soldered springs.

A device for correction of the form of upper jaw in accordance with a second variant consists of fastening elements mounted accordingly on teeth of dentition's lateral segments 11 and frontal segment 12, which are executed in the form of metal wireframes clasping teeth of dentition's corresponding segment. Plates 14 are fastened on orthodontic springs 13 soldered to the lateral fastening elements 11. Plates 14 are located on both sides of median palatine suture on convexes of the palatal fornix and connected with each other by a metal wire palatal power element 15, which is connected with a frontal segment's fastening element 12 through orthodontic springs 16.

A device for correction of the form of upper jaw in accordance with a third variant consists of fastening elements mounted accordingly on teeth of dentition's lateral segments 21 and frontal segment 22, which are executed in the form of metal wireframes clasping teeth of dentition's corresponding segment. A palatal arch 24 is fastened on orthodontic springs 23 soldered to the fastening elements 21 and 22. Plates 26 are fastened to a palatal arch 24 through orthodontic springs 25 and located on both sides of median palatine suture on convexes of the palatal fornix and may be connected with each other, in particular, by two metal wire palatal power elements 27.

In third variant of the device execution, proceeding from the clinical indications, wireframes clasping teeth of dentition's corresponding segment may be performed of components parts disposed on a separate tooth and/or group of teeth of a segment and connected with each other via lingual and/or vestibular springs In all variants of the proposed device, fastening elements are executed in the form of metal wireframes, which are performed of lingual and vestibular details located at necks of teeth from the one side and dispersedly mounted along the height of teeth from the other side and connected by crosspieces disposed in interdental spaces. At the same time, dispersedly mounted details of metal wireframes are mounted from the side of separate teeth or group of teeth facing to the movement direction.

A device for correction of the form of upper jaw in accordance with a first variant is used as follows. After fitting of the device in a cavity of mouth, the patient is trained on peculiarities of treatment with it. The device is activated through every 10-14 days.

By activation of a metal wire palatal power element (4) disposed between plates (3) and springs (2) connecting plates (3) with fastening elements of lateral segments (1) the growth of bone tissues of median palatine suture and alveolar process is achieved.

A device for correction of the form of upper jaw in accordance with a second variant is used as follows. After fitting of the device in a cavity of mouth, the patient is trained on peculiarities of treatment with it. The device is activated through every 10-14 days. By activation in sagittal and transversal directions of a palatal power element (15) disposed between plates (14) and springs (13) disposed between plates (14) and fastening elements (11) of lateral segments, as well as, springs (16) disposed between a palatal power element (15) and a fastening element (12) of a frontal segment the growth of bone tissues of median palatine suture and alveolar process is achieved.

A device for correction of the form of upper jaw in accordance with a third variant is used as follows. After fitting of the device in a cavity of mouth, the patient is trained on peculiarities of treatment with it. The device is activated through every 10-14 days. By activation in sagittal and transversal directions of springs (27) disposed between plates (26), springs (25) disposed between plates (26) and a palatal arch (24), springs (23) connecting fastening elements (21) and (22) with a palatal arch (24), the growth of bone tissues of median palatine suture and alveolar process is achieved.

The presence of zones of growth, mounting of plates above and below convex parts of the palatal fornix (in the case of a double fundus of the cupula of palate), and influence of plates on them allow to correct the form of a palate (see, FIG. 2).

Proceeding from the clinical indications second and third variants of the device may be applied in the case of malocclusion treatment.

EXAMPLE

A patient of 14 years old with complaints to cosmetic defect has been addressed. Objectively: nose breathlessness, constriction of top teeth line, cross bite, deep double fundus of the palatal fornix. The first variant of the device for correction of the form of upper jaw has made and fitted in the cavity of patient's mouth. The patient has received the necessary. recommendations on treatment with the device. After 3 months, the increase of transversal dimensions of dental alveolar process in the area of fourth teeth on 9 mm and in the area of sixth teeth on 5 mm has registered. The dental alveolar arch has corrected. The form of the cupula of palate (its geometry) has corrected. The depth of the palatal fornix in the area of the sixth teeth has decreased on 3 mm. The devices were taken off after 3 months from the beginning of the retention period, at the same time, during the retention period the device was applied within 1.5 months round the clock and within 1.5 months—only at night.

While the above is a complete description of the preferred embodiment of the present invention, it is possible to use various alternatives, modifications and equivalents. Therefore, the scope of the present invention should be determined not with reference to the above description but should, instead, be determined with reference to the appended claims, along with their full scope of equivalents. In the claims that follow, the indefinite article "A", or "An" refers to a quantity of one or more of the item following the article, except where expressly stated otherwise. Any feature, whether preferred or not may be combined with any other feature, whether preferred or not. The appended claims are not to be interpreted as including means-plus-function or step-plus-function limitations, unless such a limitation is explicitly recited in a given claim using the phrase "means for" or "step for."

What is claimed is:

1. A device for correction of the form of upper jaw comprising: fastening elements adapted to fasten on teeth of dentition's lateral segments and connected with two plates located on both sides of median palatine suture, which are connected with each other by a metal wire palatal power element, wherein the fastening elements are in the form of metal wireframes adapted to clasp teeth of dentition's lateral segments and connected with the plates through springs, wherein the plates, fastening elements and wire palatal power element are configured so that the plates contact only with convex parts of a palatal fornix of the upper jaw and exert sufficient force on mentioned convex parts to induce a rupture of a median palatine suture of the upper jaw and growth of a dental alveolar process.

2. A device for correction of the form of upper jaw containing fastening elements adapted to fasten on teeth of dentition's lateral segments and connected with two plates located on both sides of median palatine sutures, which are connected with each other by a metal wire palatal power element, and additionally containing a fastening element adapted to mount on teeth of dentition's frontal segment, wherein the fastening elements are in the form of metal wireframes adapted to clasp teeth of dentition's segments, wherein the plates are connected with the fastening elements of lateral segments through first springs, and the fastening element adapted to mount on teeth of the dentition's frontal segment is connected with the metal wire palatal power element by second springs, wherein the plates, fastening elements and wire palatal power element are configured so that the plates contact only with convex parts of a palatal fornix of the upper jaw and exert sufficient force on mentioned convex parts to induce a rupture of a median palatine suture of the upper jaw and growth of a dental alveolar process.

3. A device for correction of the form of upper jaw containing fastening elements adapted to fasten on teeth of dentition's lateral segments and connected with two plates located on both sides of median palatine suture, which are connected with each other by a metal wire palatal power element, and additionally containing a fastening element adapted to mount on teeth of dentition's frontal segment, wherein the fastening elements are in the form of metal wireframes adapted to clasp teeth of dentition's segments and connected with each other and with the plates by a palatal arch through springs, wherein the plates, fastening elements and wire palatal power element are configured so that the plates contact only with convex parts of a palatal fornix of the upper jaw and exert sufficient force on mentioned convex parts to induce a rupture of a median palatine suture of the upper jaw and growth of a dental alveolar process.

* * * * *